United States Patent [19]
> Boy et al.

[11] 4,000,049
[45] Dec. 28, 1976

[54] METHOD AND DEVICE FOR PREPARING SULPHONIC ACIDS DERIVED FROM PARAFFINIC HYDROCARBONS

[75] Inventors: Aristide Boy, Pau; Hubert Passedroit, Gan, both of France

[73] Assignee: Societe Anonyme dite: Ato Chimie, Paris, France

[22] Filed: Sept. 18, 1974

[21] Appl. No.: 507,081

[30] Foreign Application Priority Data

Sept. 20, 1973 France .................... 73.33746

[52] U.S. Cl. .................... 204/162 SA; 23/260
[51] Int. Cl.² .................... B01J 1/10
[58] Field of Search .................... 204/162 SA

[56] References Cited
UNITED STATES PATENTS

| 449,687 | 4/1891 | Maxim | 260/467 |
|---|---|---|---|
| 2,737,522 | 3/1956 | Nilsson | 260/467 |
| 3,111,538 | 11/1963 | Stow | 260/467 |
| 3,454,481 | 8/1969 | Marrian | 204/162 SA |
| 3,658,671 | 4/1972 | Nagayama et al. | 204/162 SA |
| 3,682,803 | 8/1972 | Ogata et al. | 204/162 SA |

FOREIGN PATENTS OR APPLICATIONS

| 1,474,522 | 2/1967 | France | 204/162 SA |
| 1,039,804 | 8/1966 | United Kingdom | 204/162 SA |

*Primary Examiner*—Leland A. Sebastian
*Attorney, Agent, or Firm*—Burgess Ryan and Wayne

[57] ABSTRACT

The instant invention relates to a method for preparing paraffin-sulphonic acids by photochemical sulphoxidation of paraffinic hydrocarbons. The invention also relates to a device for carrying out this method.

The invention relates more particlarly to a method for continuously preparing paraffin-sulphonic acids by photochemical sulphoxidation of paraffinic hydrocarbons comprising the steps of reacting a gaseous mixture of sulphurous acid anhydride and oxygen with a liquid paraffiaic phase and injecting at least a portion of said gaseous mixture into said liquid phase in the form of a finely divided dispersion in a recycling fraction of said paraffinic phase which carries said gaseous mixture.

6 Claims, 4 Drawing Figures

METHOD AND DEVICE FOR PREPARING SULPHONIC ACIDS DERIVED FROM PARAFFINIC HYDROCARBONS

The instant invention relates to a method for preparing paraffin-sulphonic acids by photochemical sulphoxidation of paraffinic hydrocarbons. The invention also relates to a device for carrying out this method.

Generally, paraffin sulphonic acids are prepared by the so-called "sulphoxidation process" wherein sulphurous acid anhydride and oxygen are reacted simultaneously with paraffinic hydrocarbons in the presence of photo-active radiation, especially in the presence of ultra-violet radiations.

The reaction takes place in accordance with the following equation:

$$R.H + SO_2 + H_2O + O_2 \rightarrow R - SO_3H + H_2SO_4$$

wherein R is an alkyl group.

In the known methods, the mixture of $SO_2$ and $O_2$ and the paraffins are introduced separately into the reaction zone. The gaseous mixture is introduced into the reaction medium in a form as finely divided as possible, by means of a diffuser comprising a porous sintered plate, or by means of an annular gas injector arranged at the lower end of the reaction zone. Generally, the gas flow is introduced at the lower end of the reactor under a pressure sufficient to overcome the pressure of the liquid column, said gas flow being divided into extremely small bubbles. However, the porous sintered plates as well as the annular gas injectors or similar distributers provided with orifices do not allow to achieve, or to maintain, the desired division of the gas in the liquid paraffinic phase.

More particularly, in the case where plates or discs are used, the gas distribution efficiency is limited on account of the absence of stirring or agitation. Furthermore, the bubbles thus obtained have a diameter substantially greater than that of the diffusion pores, the small dimensions of which promote or facilitate the joining or coalescence of the small bubbles. It should also be noted that the pressure required for overcoming the pressure of the liquid column must be comparatively high so as to allow to overcome the resistance to the flow of gas within the porous material. Furthermore, the latter exhibits a pronounced trend to superficial obstruction.

As regards the distributors comprising orifices, the manufacture of which is rather intricate, they impart, like the porous diffusors, an agitation which is extremely reduced or even nil; this considerably reduces the efficiency of the distribution of the gas in the liquid.

It is in fact practically impossible to use conventional agitating or stirring devices (such as turbines or discs provided with vanes, bladed wheels, impellers, etc.), on account of the fact that these devices generate vibrations which greatly increase the risk of breakage of the glass or quartz elements of the photo-chemical reactor.

Consequently, in the conventional methods, the sulphoxidation reaction cannot be carried out under favorable conditions, due to the poor gas transfer rate, especially the poor transfer rate of the oxygen, in the paraffin.

It is an object of the instant invention to overcome these drawbacks of the known methods and to provide a novel method by which a more satisfactory transfer of the reagents from the gaseous phase to the liquid phase is achieved.

The novel method for the continuous preparation of paraffin-sulphonic acids by photochemical sulphoxidation of paraffinic hydrocarbons comprises reacting a gaseous mixture of sulphurous acid anhydride and oxygen with a liquid paraffinic phase, in which method a portion of said gaseous mixture is injected into the liquid phase in the form of a finely divided dispersion in a recycled fraction of the paraffinic phase which carries the gaseous mixture.

This injection of the reagents into the reaction zone facilitates the transfer of the oxygen, as well as the recirculation and the agitation of the reaction medium, without generating undesirable, or even dangerous, vibrations.

The instant invention also relates to a device for carrying out the aforesaid method.

It is thus another object of the instant invention to provide a device wherein the injection of the gaseous mixture into the reactor containing the paraffinic phase is achieved by means of at least one hydro-injector comprising, in a manner known per se, at least one inlet orifice for the actuating fluid, at least one suction orifice and at least one discharge orifice, said discharge orifice opening into the reactor, said suction orifice being connected to inlet means for admitting fresh or recycled gaseous mixture of sulphurous acid anhydride and oxygen, said inlet orifice for the actuating fluid being connected to the conduits serving to recycle the reaction medium and/or to supply fresh paraffins.

In the embodiment wherein the suction orifice is connected to the reaction zone containing the gaseous phase, this manner of introduction is furthermore advantageous in that it allows the recycling of the gaseous reagents to be effected without the use of a compressor.

These and other objects and features of the instant invention will become apparent from the following description and the appended drawings which exemplify the invention, but are not to be construed as limiting the scope thereof.

Figure 1:
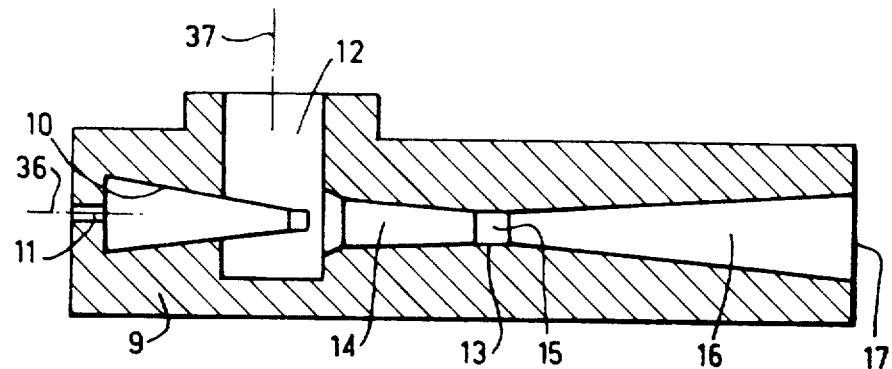
FIG. 1 is a schematic view of an embodiment of the hydro-injector which may be used in the device for carrying out the method according to the instant invention.

Referring, more particularly, to FIG. 1, which shows schematically a hydro-injector 9 adapted to be used for carrying out the method of the present invention, it will be seen that said hydro-injector comprises an actuating nozzle 10 into which the pressurized actuating fluid is delivered through an inlet orifice 11. This actuating nozzle comprises a converging portion which is terminated by a neck portion and opens into a chamber, or suction chimney 12, connected to a source of the gas to be aspirated.

Coaxially with nozzle 10 and opening into suction chamber 12, an expansion nozzle 13 is arranged which comprises a converging or mixing portion 14 wherein the actuating fluid which has been accelerated in nozzle 10 is atomized, the potential energy of said fluid being transformed into speed, i.e. into kinetic energy.

Within said mixing portion of nozzle 13 the momenta are transferred between the actuating fluid and the aspirated gas in such a way that at the outlet of said mixing portion of nozzle 13 the speed of both said fluids is homogeneous.

The mixing portion 14 is followed by a diffuser neck 15 and a diverging diffuser 16 wherein the speed is transformed into pressure, which is achieved by means of a discharge orifice 17. As will be described in greater detail hereinbelow this orifice 17 opens into the reactor.

Figure 2:
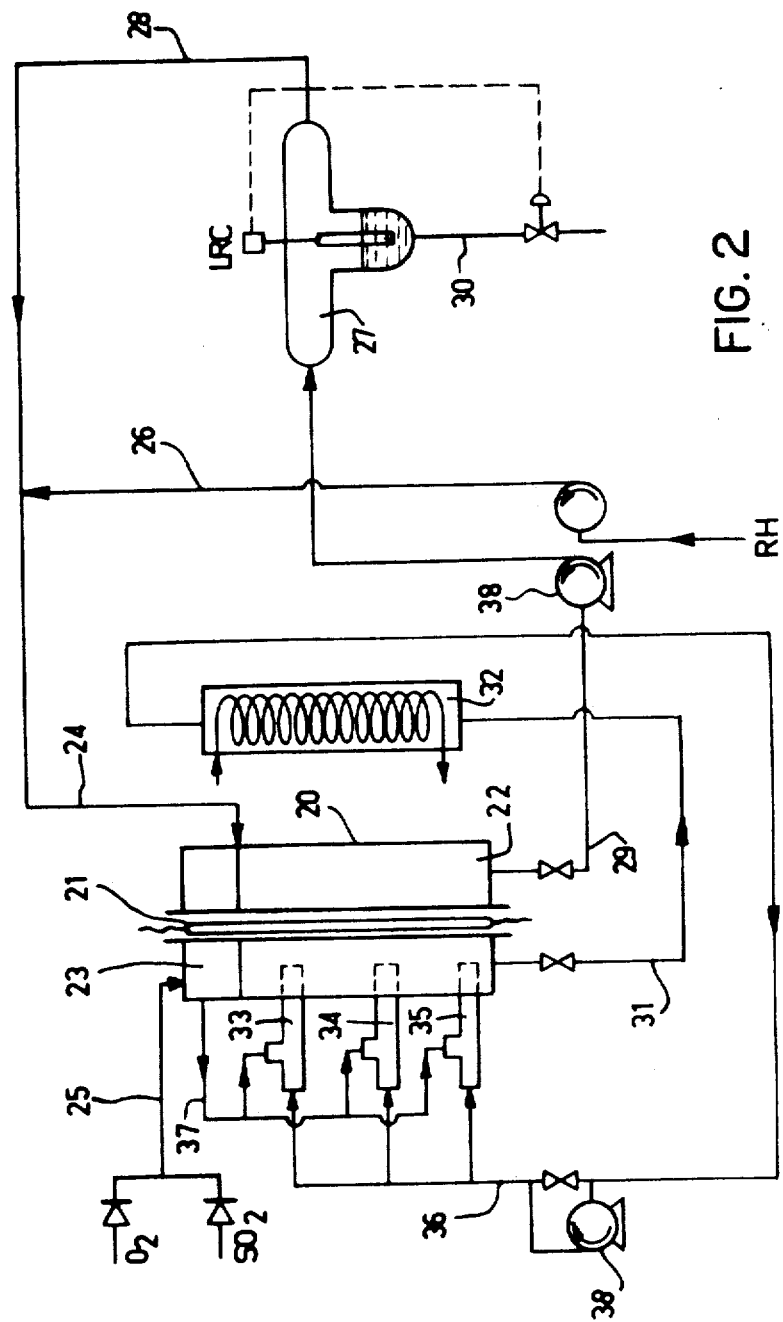
FIG. 2 is a schematic view of the reaction section of said device.

FIG. 2 shows schematically one embodiment of the device for carrying out the photochemical sulphoxidation in accordance with the present invention.

This device comprises a cylindrical reactor 20 and a lamp 21 adapted to generate ultraviolet radiation and arranged in a coaxial position inside said reactor; this lamp may be a mercury vapour lamp the main spectral emission lines of which are 3020 A, 3130 A, 3650 A and 4047 A.

Cylindrical reactor 20 contains a paraffinic liquid phase 22 above which is located a gaseous phase 23, said phases being supplied, respectively, by supplying circuits or conduits 24 and 25; the gaseous phase 23 consists of a mixture containing, in appropriate relative amounts, sulphurous acid anhydride and oxygen, while the liquid phase or paraffinic phase 22, is constituted in part by fresh paraffins supplied by an inlet conduit 26, and in part by a light fraction containing paraffin and less than 3% of sulphonic acid supplied through a conduit 28 from a decanter 27 into which the reaction medium is introduced through a conduit 29 comprising a pump 38.

In decanter 27 the heavy fraction constituting a solution of sulphonic acid and sulphuric acid is extracted through a conduit 30 and then treated, e.g. according to the process described in the applicant's French Patent Specification, No. 2,102,540 (National Registering number 70.29,211), filed on Aug. 7, 1970 and relating to the separation of sulphonic acids.

The liquid phase in reactor 20 contains a convenient quantity of water supplied by a conduit (not shown in the drawing); the homogenization of the liquid phase and the gaseous phase in said reactor is achieved by means of a liquid recycling circuit 31 which comprises a condenser, or cooler 32 adapted to eliminate from the paraffinic solution which flows through said cooler the calories generated by lamp 21 and by the exothermic nature of the reaction.

This recycled paraffinic solution is delivered to injectors three of which (33, 34, 35) are used in the example shown; said injectors are similar to injector 9 described with reference to FIG. 1. The respective discharge orifices 17 of said injectors open into the mass of liquid phase contained in reactor 20, at different levels of said reactor, while the respective suction orifices of said injectors are connected by a conduit 37 to the gaseous phase 23 in the top portion of the reactor.

Figure 3:
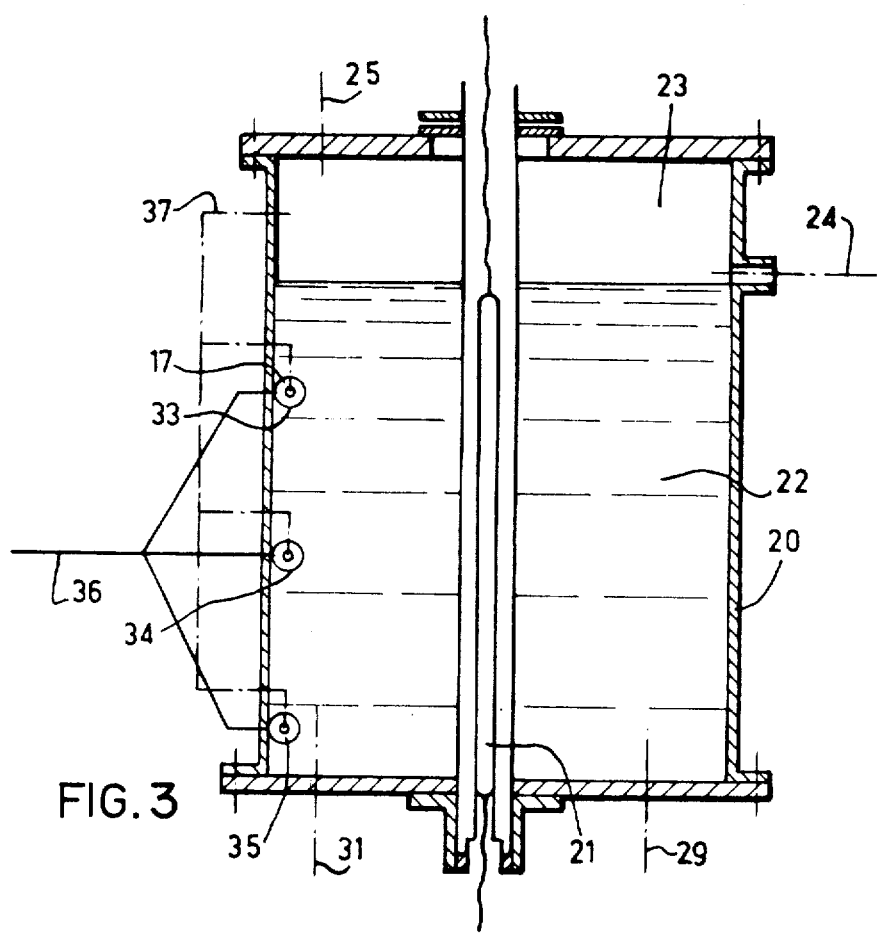
FIG. 3 shows an arrangement of the hydro-injectors in the above-mentioned device.

FIG. 3 shows in more detail the reactor 20 and the injectors 33, 34, 35 which are arranged in such a manner that the respective axes of their discharge orifices are substantially tangential to the wall of the reactor.

Due to this arrangement and to the location of the injectors on different levels of the reactor, a homogeneous agitation and an increase of the turbulence zones are obtained, whereby the transfer of the oxygen to the paraffin is particularly enhanced.

Figure 4:
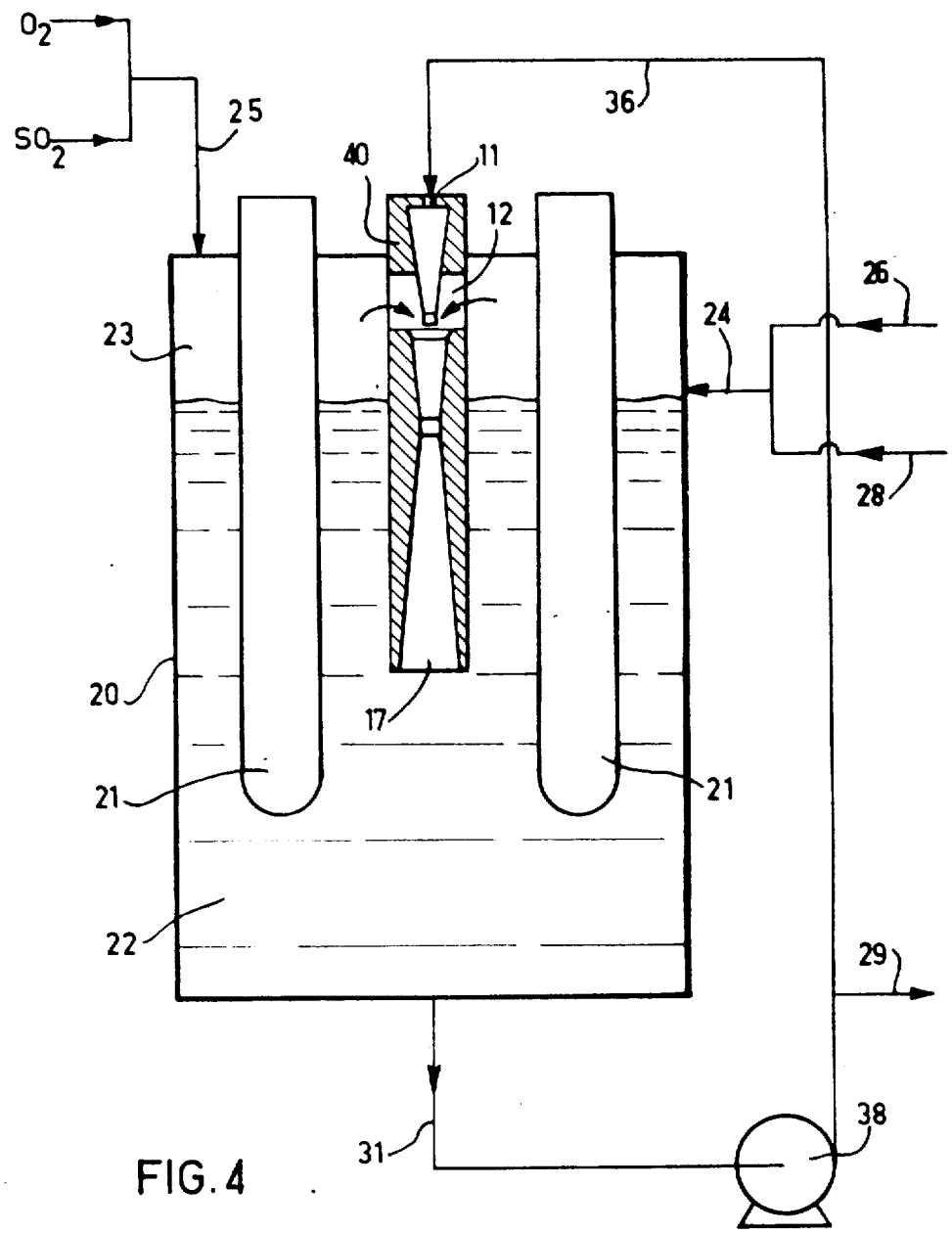
FIG. 4 is a schematic view of another embodiment comprising a reactor equipped with the hydro-injector which may be used in the device shown in FIG. 2.

It is obvious that other arrangements of the hydro-injector, or hydro-injectors, provided in the reactor may be used. For instance, as shown in FIG. 4, it is possible to use a hydro-injector 40 similar to the hydro-injector shown in FIG. 1, in an arrangement wherein the axis of the discharge orifice coincides with, or is parallel to, the axis of the reactor 20, which latter contains, as described hereinabove, a liquid paraffinic phase 22 (comprising a convenient amount of water), and a reactive gaseous phase 23 above said liquid phase, while a plurality of lamps 21 are symmetrically arranged so as to surround said hydro-injector. The inlet opening 11 of said hydro-injector is connected to a conduit 36 which supplies the pressurized actuating fluid constituted by a fraction of the reaction medium drawn off by conduit 31 and then introduced into conduit 36 by means of a pump 38. One of the conduits 31 and 36 may also be provided with a condenser or cooler (not shown in the drawing). A duct 29 is mounted on conduit 36 for drawing off a portion of the reaction medium drawn off by conduit 31, said drawn-off portion being treated as described hereinabove with reference to FIG. 2, with a view to separating the paraffins and the aqueous phase containing the sulphonic acids, the aqueous phase being then treated with a view to extracting the sulphonic acids by any convenient method.

The hydro-injector is mounted in the reactor in such a manner that its discharge orifice 17 is located below the free surface of the liquid phase 22 and that the apertures of the suction chamber 12 of said injector are located in the zone of the reactor which contains the gaseous reaction phase 23.

The gaseous reaction phase (mixture of oxygen and $SO_2$) is supplied to the reactor by a conduit 25, while the paraffinic phase which is constituted in part of fresh paraffins delivered by conduit 26, and in part by the paraffins which have been separated from the aqueous sulphonic phase and recycled through conduit 28, is introduced into the reactor 20 by conduit 24.

The paraffins used in the process according to the present invention contain 7 to 30 carbon atoms, and preferably 10 to 20 carbon atoms.

The reactive gaseous mixture of $SO_2$ and $O_2$ is used in a molar ratio of $SO_2:O_2$ varying between 1:1 and 20:1, said molar ratio being preferably equal or substantially equal to about 2:1, which ratio corresponds to the stoichiometrical ratio.

The reaction is carried out at a temperature varying between 0° and 80° C, preferably between 10° and 50° C, and under a relative pressure of 0 to 20 (or more) atmospheres; preferably said pressure varies between 0 and 5 atmospheres.

As it has already been stated, the reaction mixture issuing from the reactor is delivered, at least in part (FIG. 2), to a decanter where a portion of the paraffin is separated from the aqueous phase containing the sulphonic acids, whereafter the thus separated paraffin is recycled by reintroducing the same into the reaction zone.

The raw aqueous phase containing the sulphonic acids is treated by methods known per se, and preferably, for instance, by the method described in the above mentioned French Patent Specification, with a view to separating the sulphonic acids.

Tests and measurements effected while using the device described hereinabove have shown an obvious improvement in the production, especially due to an increase of the oxygen transfer capacity of a sulphoxidation installation which is provided, in accordance with the present invention, with hydro-injectors, as compared to conventional installations provided with porous distributors or other distributors comprising orifices for introducing the reactive gaseous mixture.

This improvement is shown by the following examples which are not to be construed as limiting in any way the scope of the instant invention:

EXAMPLE 1

The device or installation used corresponds to the one described with reference to FIGS. 1 to 3.

The paraffin phase used was a commercial blend containing normal paraffins containing 14 to 17 carbon atoms. The reactive gaseous mixture used was a mixture of $SO_2$ and oxygen in a molar ratio of $SO_2:O_2 = 2:1$.

The reaction was carried out at a temperature of 35° C while a relative pressure of 0.1 atmosphere was maintained in the reactor, three quarters of which were filled with paraffin, whereas the remaining quarter, at the top of the reactor, was filled with the reactive gaseous mixture.

Three hydro-injectors were mounted along the vertical wall of the reactor and regularly spaced in the vertical direction, starting from the bottom of the reactor.

A total flow of 6.4 cubic meters/hour of reaction medium was recycled toward the three injectors. This flow rate of reaction medium corresponds to a total flow rate of 25 cubic meters/hour of recycled reactive gaseous mixture.

When the reaction zone was subjected to a regular irradiation by an ultra-violet radiation emitting system having an effective power of 650 watts, an output of paraffin sulphonic acid of 95 moles/hour was achieved. The quantity of sulphonic acid produced within the same time interval was about 95 moles/hour. The consumption of $SO_2$ and $O_2$ corresponded substantially to the stoichiometric data of the reaction.

EXAMPLE 2

This example is given as a comparative example related to the prior art. When this example was carried out the device used in Example 1 had been modified by withdrawing the hydro-injectors and by replacing the same with a plate of sintered stainless steel which was arranged at the bottom of the reactor and through which the reactive gaseous mixture of $SO_2$ and oxygen (molar ratio $SO_2:O_2 = 2:1$) was injected, the diameter of which plate was slightly smaller than that of the reactor.

The flow rate of the reactive gaseous mixture injected through the porous plate was equal to about three times the flow rate corresponding to the stoichiometric date of the reaction, while the other operating data, such as lighting (i.e. irradiation), temperature, and paraffin flow rate, were the same as those indicated in Example 1 hereinabove.

Under these operating conditions, the output of paraffin sulphonic acid was only 42 moles/hour.

EXAMPLE 3

The same operating conditions as those described in Example 1 were applied; however, only two hydro-injectors were used with a total flow rate of actuating liquid (reaction mixture) of 4.8 cubic meters/hour, which led to a flow rate of 14 cubic meters/hour of recycled reactive gaseous mixture.

The output of paraffin-sulphonic acid was 64 moles/hour.

EXAMPLE 4

The operating conditions were similar to those described with reference to Example 1 hereinabove; however only one hydro-injector was used. The actuating fluid flow rate was 2.4 cubic meters/hour, which led to a reactive gaseous mixture flow rate of 9 cubic meters/hour.

45 moles/hour of paraffin sulphonic acid were obtained.

While particular embodiments of the present invention have been shown and described hereinabove, it will be appreciated by those skilled in the art that other equivalent techniques may be suggested. The appended claims cover all such changes and modifications and are deemed to define the true scope of the instant invention.

What is claimed is:

1. In a method for continuously preparing paraffin sulphonic acids by photochemical sulphoxidation of paraffinic hydrocarbons by contacting in a reaction zone a liquid paraffinic phase with a gaseous mixture of sulphurous acid anhydride and oxygen in the presence of photochemical radiations, the improvement comprising the steps of:
   a. injecting said gaseous mixture into said liquid paraffinic phase in the reaction zone in the form of a finely divided dispersion in a fraction of said liquid paraffinic phase
   b. withdrawing a fraction from said liquid paraffinic phase in the reaction zone
   c. finely dispersing said gaseous mixture in said liquid fraction, and
   d. recycling into said liquid phase contained in said reaction zone the resulting finely divided dispersion thus formed of said gaseous mixture in said fraction.

2. The method of claim 1, wherein the improvement comprises the steps of:
   a. withdrawing a fraction from said liquid paraffinic phase in the reaction zone, at a rate ranging from about 2.4 cm/hour to about 6.4 cm/hour,
   b. finely dispersing said gaseous mixture in said liquid fraction, and
   c. recycling into said liquid phase contained in said reaction zone the resulting finely dispersion thus formed of said gaseous mixture in said fraction.

3. The method of claim 1, wherein the improvement comprises the steps of:
   a. withdrawing a fraction from said liquid paraffinic phase in the reaction zone, at a rate ranging from about 2.4 cm/hour to about 6.4 cm/hour,
   b. finely dispersing said gaseous mixture in said liquid fraction so that the amount of gaseous mixture dispersed in the liquid fraction ranges from about 4.8 cm/hour to 25 cm/hour, and
   c. recycling into said liquid phase contained in said reaction zone the resulting finely dispersion thus formed of said gaseous mixture in said fraction.

4. The method of claim 3, wherein said fraction is withdrawn at a rate of about 6.4 cm/hour and the gaseous mixture is dispersed in said fraction at a rate of about 25 cm/hour.

5. The method of claim 3, wherein said fraction is withdrawn at a rate of about 4.8 cm/hour and the gaseous mixture is dispersed in said fraction at a rate of about 14 cm/hour.

6. The method of claim 3, wherein said fraction is withdrawn at a rate of about 2.4 cm/hour and the gaseous mixture is dispersed in said fraction at a rate of about 9 cm/hour.

* * * * *